United States Patent [19]

Pastor et al.

[11] Patent Number: 5,276,076
[45] Date of Patent: Jan. 4, 1994

[54] AMORPHOUS SOLID MODIFICATION OF 2,2',2''-NITRILO[TRIETHYL-TRIS-(3,3',5,5'-TETRA-TERT-BUTYL-1,1'-BIPHENYL-2,2'-DIYL)PHOSPHITE]

[75] Inventors: Stephen D. Pastor, Danbury, Conn.; Sai P. Shum, Hawthorne, N.Y.

[73] Assignee: Ciba-Geigy Corporation, Ardsley, N.Y.

[21] Appl. No.: 983,186

[22] Filed: Nov. 30, 1992

[51] Int. Cl.⁵ .............................................. C08K 5/51
[52] U.S. Cl. .................................... 524/119; 558/78
[58] Field of Search ......................... 524/119; 558/78

[56] References Cited

U.S. PATENT DOCUMENTS

| | | | |
|---|---|---|---|
| 4,318,845 | 3/1982 | Spivack et al. | 524/91 |
| 4,374,219 | 2/1983 | Spivack et al. | 524/91 |

OTHER PUBLICATIONS

Morrison et al. *Organic Chemistry*, Third Edition Allyn and Bacon, Inc. Boston, pp. 26 & 27, 1978.

*Primary Examiner*—Kriellion S. Morgan
*Attorney, Agent, or Firm*—Luther A. R. Hall

[57] ABSTRACT

The amorphous solid modification of 2,2',2'''-nitrilo[triethyl-tris-(3,3',5,5'-tetra-tert-butyl-1,1'-biphenyl-2,2'-diyl)phosphite] is obtained by melting said compound and rapidly cooling the melt.

The amorphous solid is an effective process stabilizer for polyolefins, particularly polypropylene.

6 Claims, No Drawings

AMORPHOUS SOLID MODIFICATION OF 2,2',2''-NITRILO[TRIETHYL-TRIS-(3,3',5,5'-TETRA-TERT-BUTYL-1,1'-BIPHENYL-2,2'-DIYL)PHOSPHITE]

This invention pertains to an amorphous solid modification of 2,2',2''-nitrilo[triethyl-tris-(3,3',5,5'-tetra-tert-butyl-1,1'-biphenyl-2,2'-diyl) phosphite] and to a process for preparing said modification.

BACKGROUND OF THE INVENTION 2,2',2''-Nitrilo[triethyl-tris-(3,3',5,5'-tetra-tert-butyl-1,1'-biphenyl-2,2'-diyl) phosphite] is a compound having the formula I

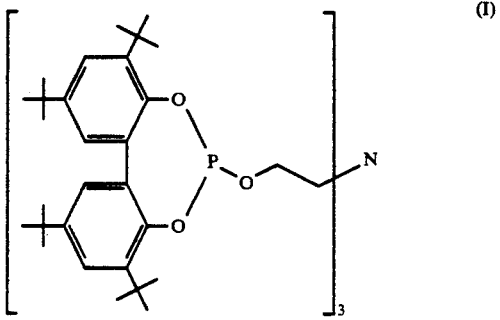

This compound of formula I is useful as a processing stabilizer for organic polymers as taught in U.S. Pat. Nos. 4,318,845 and 4,374,219. The compound of formula I is disclosed as being a white powder melting at 121°-134° C. The relatively high melting point of the "white powder" form of the compound of formula I as disclosed in the above mentioned patents is a problem when stabilizing organic polymers processed at relatively low temperatures such as blow molding of HDPE and processing of natural rubber. The result is the additive is not uniformly distributed within the organic polymer causing problems in the stabilization performance of the additive stabilizer.

In accordance with the present invention an amorphous form of the compound of formula I is obtained which does not suffer the problems associated with the higher melting powder reported previously. This new amorphous form is characterized by a glass transition temperature ($T_g$) within the range of from 105°-110° C. free of any endothermic melting peak above 110° C. up to 230° C. as determined by differential scanning calorimetry (DSC). Additionally the amorphous form of the present invention gave a featureless X-ray diffraction pattern obtained using Cu-K$\alpha$.

The instant invention also relates to a process for the preparation of this novel amorphous solid modification of the compound of formula I.

The instant invention also pertains to a composition stabilized against thermal, oxidative and actinic induced degradation which comprises
(a) a polyolefin, and
(b) an effective amount of the amorphous solid form of 2,2',2''-nitrilo[triethyl-tris-(3,3',5,5'-tetra-tert-butyl-1,1'-biphenyl-2,2'-diyl)phosphite], characterized by melting in the range of 105°-110° C. and by an X-ray diffraction pattern which is featureless.

Preferably, the polyolefin is polypropylene.

The instant amorphous solid modification is obtained from any of the solid forms of the compound of formula (I) by melting the compound and rapidly cooling the melt. The preferred method consists of pouring the molten material onto a cool surface maintained below 100° C., more preferably near 25° C. The amorphous solid thus obtained may be further ground or granulated into any desired particle size by conventional means.

Differential scanning calorimetry (DSC) measurements are obtained on a TA Instrument Inc., 910 differential calorimeter, with a 100 mL/min nitrogen purge, aligned aluminum pan, temperature scan at 5° C./min to 230° C.

X-ray diffraction patterns are recorded on a Philip Norelco X-ray Diffractometer unit, using Cu-K$\alpha$ radiation with a nickel filter.

EXAMPLE 1

The compound of formula I,2,2',2''-nitrilo[triethyl-tris-(3,3',5,5'-tetra-tert-butyl-1,1'-biphenyl-2,2'-diyl) phosphite], is prepared according to procedure of Example 4 of U.S. Pat. No. 4,318,845. The compound of formula I is heated at 210° C. until a clear melt is obtained. The melt is cooled rapidly to ambient temperature to yield a glassy solid with $T_g$(DSC) of 105°-110° C. The white solid is conveniently ground into a white powder using a mortar and pestle. The X-ray diffraction pattern obtained using Cu-K$\alpha$ is featureless.

Analysis: Calcd for $C_{90}H_{132}NO_9P_3$: C,73.8;H,9.1;N,0.96. Found: C,73.4;H,9.3;N,0.9.

EXAMPLE 2

BULK DENSITY

This example illustrates the superior packaging properties of the novel amorphous solid modification of the compound of formula I as prepared in Example 1 as compared to the powder form of the compound of Example 4 of U.S. Pat. No. 4,318,845.

The apparent bulk density of the solids is measured according to the method of ASTM D-1895(79). A higher apparent bulk density allows for a greater mass per unit volume which affords advantages in packaging of the solid product, such as lower costs for the packaging material, less storage space is required, etc.

| Compound of | Bulk Density (g/mL) |
| --- | --- |
| Example 1 (amorphous solid form | 0.49 |
| Example 4 of U.S. Pat. No. 4,318,845 (prior art) | 0.44 |

EXAMPLE 3

PROCESS STABILIZATION OF PROPYLENE AT 525° F. (274° C.)

When unstabilized polypropylene containing 0.075% by weight of calcium stearate is admixed with an effective amount of the amorphous solid of Example 1 and then extruded from an extruder at 525° F. (274° C.), the melt flow rate (in grams/10 minutes) is determined by ASTM method D1238.

The instant amorphous compound is particularly effective in stabilizing polypropylene against thermal and oxidative degradation as shown by a minimum change in the melt flow rate.

What is claimed is:

1. A process for the preparation of the amorphous solid form of the compound 2,2',2''-nitrilo[triethyl-tris-(3,3',5,5'-tetra-tert-butyl-1,1'-biphenyl-2,2'-diyl) phosphite] which comprises melting said compound and rapidly cooling the melt.

2. A process according to claim 1 which comprises pouring the molten material onto a cool surface maintained below 100° C.

3. A process according to claim 2 wherein the cool surface is near 25° C.

4. The amorphous solid form of 2,2',2''-nitrilo[triethyl-tris-(3,3',5,5'-tetra-tert-butyl-1,1'-biphenyl-2,2'-diyl) phosphite], characterized by melting in the range of 105°-110° C. and by an X-ray diffraction pattern which is featureless.

5. A composition stabilized against thermal, oxidative and actinic induced degradation which comprises
   (a) a polyolefin, and
   (b) an effective amount of the amorphous solid form of 2,2',2''-nitrilo[triethyl-tris-(3,3',5,5'-tetra-tert-butyl-1,1'-biphenyl-2,2'-diyl) phosphite], characterized by melting in the range of 105°-110° C. and by an X-ray diffraction pattern which is featureless.

6. A composition according to claim 5 wherein the polyolefin is polypropylene.

* * * * *